United States Patent [19]

Henry et al.

[11] Patent Number: 5,730,765
[45] Date of Patent: Mar. 24, 1998

[54] SUPER TOXIC ANALYTICAL GLOVE BOX SYSTEM

[75] Inventors: Charles E. Henry; Monica J. Heyl, both of Joppa; Dennis J. Reutter, Churchville, all of Md.

[73] Assignee: The United States of America as represented by the Secretary of the Army, Washington, D.C.

[21] Appl. No.: 772,053

[22] Filed: Dec. 5, 1996

Related U.S. Application Data

[60] Provisional application No. 60/016,814, Apr. 10, 1996.

[51] Int. Cl.$^6$ .................................................. B01D 15/08
[52] U.S. Cl. .................. 55/270; 55/274; 55/385.2; 55/385.4; 55/472; 55/DIG. 18; 96/101; 454/184
[58] Field of Search ........................ 55/357, 270, 274, 55/472, 385.1, 385.2, 385.4, 385.6, DIG. 18, DIG. 34; 96/101, 105, 106; 73/19.02, 23.22, 23.35, 23.42; 454/58, 61, 63, 184

[56] References Cited

U.S. PATENT DOCUMENTS

| | | | |
|---|---|---|---|
| 1,642,577 | 9/1927 | Carson | 55/DIG. 18 |
| 2,243,999 | 6/1941 | Chapple | 55/385.2 |
| 2,616,414 | 11/1952 | McPherson | 55/385.2 |
| 3,464,388 | 9/1969 | Stout | 55/DIG. 18 |
| 3,473,876 | 10/1969 | Steinberg | 55/270 |
| 3,777,736 | 12/1973 | Van Der Waaij et al. | 55/385.2 |
| 4,704,951 | 11/1987 | Pruchon | 55/385.2 |
| 4,883,505 | 11/1989 | Lucero | 55/270 |
| 5,083,558 | 1/1992 | Thomas et al. | 55/DIG. 18 |
| 5,087,360 | 2/1992 | Wright et al. | 96/101 |

*Primary Examiner*—C. Scott Bushey
*Attorney, Agent, or Firm*—Ulysses John Biffoni

[57] ABSTRACT

An Analytical Glove Box System has a sealed instrumentation enclosure, a glove box having an injection port coupled to the instrumentation and an air lock through which sample vials can be passed from outside into the glove box. A pump is provided for withdrawing gas from the glove box enclosure through a filter system so that the glove box is maintained at a negative pressure with respect to ambient. Toxic chemical samples can thus be safely handled by an operator and analyzed with sophisticated instrumentation without the risk of contamination. All effluent from the glove box is filtered before release to ambient, leakage from the glove box is further eliminated due to the negative pressure differential maintained, and the instruments are isolated from the potentially contaminated environment of the glove box. The system further provides the ability to conduct highly toxic chemical analysis in field locations since it is portable (including air transportable) and is easily decontaminated.

12 Claims, 2 Drawing Sheets

SUPER TOXIC ANALYTICAL GLOVE BOX SYSTEM

GOVERNMENTAL INTEREST

The invention described herein may be manufactured, used and licensed by or for the United States Government.

This application is a continuation of United States provisional application Ser. No. 60/016,814 filed on Apr. 10, 1996.

FIELD OF THE INVENTION

The field of the invention is the detection and analysis of toxic matter. More particularly, the present invention relates to portable analytical systems used to analyze highly toxic chemical samples.

BACKGROUND OF THE INVENTION

At the present time, highly toxic materials such as HD (mustard gas), and VX and GB (nerve gases) which are used in chemical warfare are destroyed by incineration, but alternative methods such as chemical neutralization followed by biodegradation are under investigation. In order to evaluate the efficiency of the-disposal methods under investigation, it is necessary to carry out a purity analysis of the chemicals involved as they occur at a storage site and as the disposal process proceeds. At present, this is accomplished by taking samples from the site to a laboratory and utilizing expensive instruments such as a gas chromatograph, GC, and a mass selective detector, MSD, for analysis.

The instruments are placed in a fume hood, and an operator transfers chemicals to be analyzed from a sample container to the injection port of an instrument. Because of the likelihood of undetected spills that would contaminate the instruments, the instruments are in effect dedicated to this operation because decontaminating the instruments usually destroys them. Thus, once used for analysis of HD or VX, the instruments are not available for any other use.

SUMMARY OF THE INVENTION

In accordance with this invention, a portable laboratory is provided in which the expensive analytical instruments are located in a sealed analytical compartment that interfaces with a glove box (where the samples are handled by an operator) only by an injection port leading to a separation column and exhaust tubes from the instruments. The analytical instruments are thereby isolated from the potentially contaminated glove box enclosure. Vials of chemicals to be analyzed are introduced into the glove box via a double door airlock and loaded by the gloved hands of an operator into an injection port that is coupled to the separation column, so that minute samples can be fed to the isolated analytical instruments.

The glove box is maintained at a pressure slightly less than atmospheric pressure by provision of a valved inlet port that is open to the atmosphere and an exhaust port that is coupled by a filter to a vacuum pump. The filter and vacuum pump are mounted in a separate filter chamber. Thus, any chemical spilled while loading it into the injection port and any chemicals passing through the analytical instruments are quickly removed from the glove box via a filter and can not come in contact with the analytic instruments, or the operator of that equipment.

The portable laboratory is also designed with features to facilitate easy and rapid setup, tear down, decontamination, certification of non-toxicity for air transport, repeated packaging for shipments, and the protection of sensitive analytical equipment.

It is, therefore, an object of the present invention to provide a field-portable analytical glove box system which isolates the highly toxic chemical samples being analyzed from the analytical instruments as well as from the operator and environment.

DETAILED DESCRIPTION OF THE INVENTION

Figure 1:
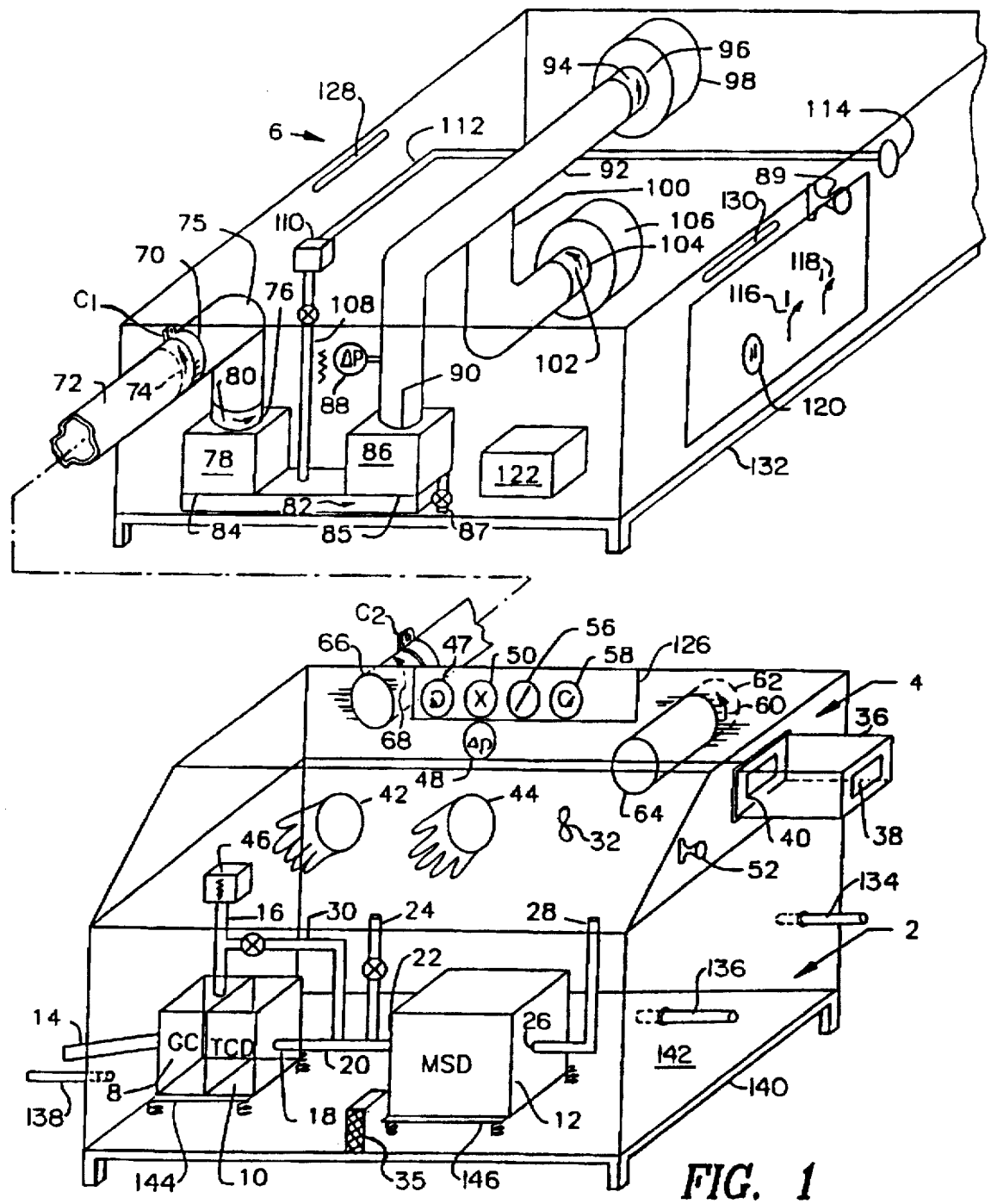
FIG. 1 is an isometric projection showing the locations of various components of the system of the invention.
Figures 2, 3:
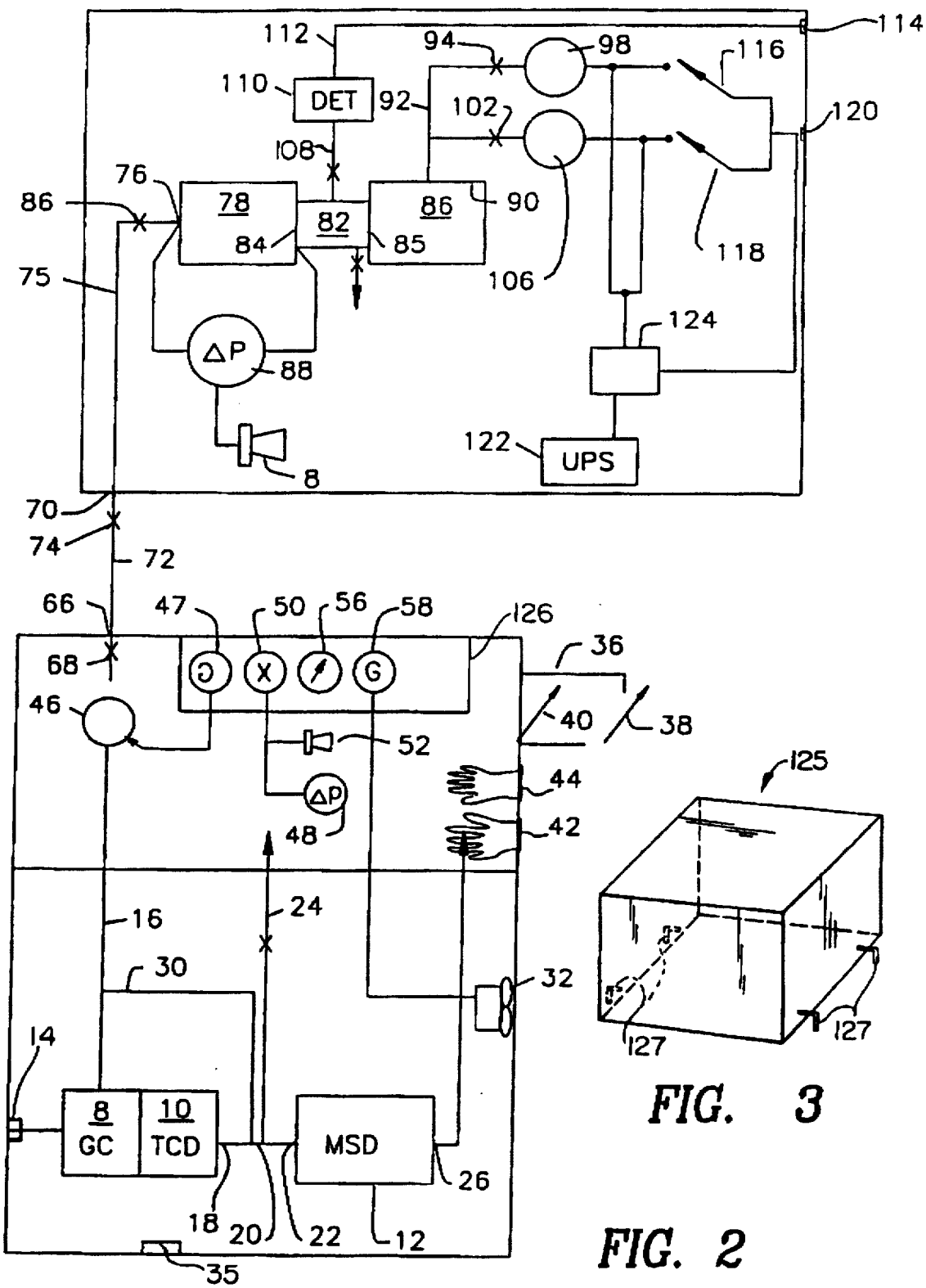
FIG. 2 is a schematic functional representation of the system of the invention showing certain interconnections not shown in FIG. 1.
FIG. 3 is an isometric projection of a cover for the glove box and analytical compartment.

In the description, like components in FIGS. 1 and 2 will be designated in the same way. In FIG. 1, the enclosures are drawn as though they were transparent.

As shown in FIG. 1, the super toxic analytical glove box system of the invention, hereinafter referred to as STAG, is comprised of three sections, an analytical instrument compartment 2, a glove box 4 and a filter module 6.

In this particular embodiment of the invention, the analytical compartment 2 contains a gas chromatograph, (GC) 8, a thermal conductivity detector, (TCD) 10, and a mass selective detector, (MSD) 12. Carrier gas for the gas chromatograph, GC 8 is supplied from an external source, not shown, via a tube 14. One end of a separation column 16 for the GC 8 projects upwardly out of the analytical compartment 2 and into the glove box 4. Although not shown, the other end of the separation column 16 is coupled to the input of the TCD 10. The outlet port 18 of the TCD 10 is coupled via a tube 20 to the input port 22 of the MSD 12, and a valved exhaust line 24 extends from the tube 20 into the glove box 4. An exhaust port 26 of the MSD 12 is connected via a tube 28 to the interior of the glove box 4. A valved tube 30 within the analytical compartment 2 is connected between the separation column 16 and the tube 20. Thus by operation of the valves, analyte in the first part of the separation column 16 can be directed to the GC 8 or the inlet port 22 of the MSD 12, and, if desired, it can be caused to flow to the MSD 12 via the GC 8 and the TCD 10 as they do not destructively alter the analyte.

The analytic compartment 2 is cooled by a temperature controlled fan 32 that draws air from ambient through a HEPA filter 35 into the analytical compartment 2, around the GC 8, the TCD 10, and the MSD 12 and back out to ambient at the fan 32.

The glove box 4 sits on the analytic compartment 2 and is provided with an airlock 36 having sequential doors 38 and 40 that can be manually operated. A vial of analyte is introduced into the airlock 36 via the door 38 while the door 40 is closed, and it is moved into the glove box 4 via the door 40 while the door 38 is closed. Operation of the door 40 is accomplished by an operator's hand in gloves having their wrist sections sealed around openings 42 and 44 respectively. With his gloved hands, an operator opens the vial and injects a minute amount of analyte contained in it into a septum of an injection port 46 that is connected to the end of the separating column 16 that is in the glove box 4. As will be explained in connection with FIG. 2, the temperature of the injection port 46 is controlled by an electric heater which wraps around the port 46 and maintains it at whatever temperature is set on a controller 47.

A differential pressure detector and gauge 48 operates a light 50 and a buzzer 52 so as to give a quick warning of a change in the pressure within the glove box 4, the pressure being maintained in a manner to be explained and indicated by the gauge 48 that may be a magnihelic differential pressure gauge. The temperature of the analytic compartment 2 is indicated by a gauge 56, and the fan 32 is controlled by a controller 58 so as to draw heat from the analytical compartment 2 thereby cooling the GC 8 and the (TCD) 10, and maintaining the temperature at a desired value. The only source of heat within the analytical compartment 2 is the GC 8 and the MSD 12.

Although the glove box 4 is sealed, leakage of gas therefrom is inhibited by maintaining it at a pressure that is below atmospheric pressure by one half an inch of water, for example. This also prevents leakage through the airlock 36. In this embodiment of the invention, this is accomplished by drawing air through the glove box 4 at a controlled rate. Flow of air through an input port 60 is controlled by an external manually operable valve 62, and the air is filtered by a filter 64, a HEPA filter, and flow of air through an outlet port 66 is controlled by a manually operable valve 68. The flow is induced by drawing a vacuum on the outlet port 66 by the filter module 6 in a manner to be explained.

Coupling between the outlet port 66 of the glove box 4 and an inlet port 70 of the filter module 6 is via a flexible tube 72 and an external manually operable valve 74. One end of the tube 72 is removably attached to the valve 74 by an encircling spring damp $C_1$ and its other end is removable to the outlet port 66 by a spring damp $C_2$. A tube 75 within the filter module 6 couples its inlet port 70 to the inlet port 76 of a filter that, for example, may be an M48 nuclear biological chemical filter 78 via a manually operable valve 80. A plenum 82 connects the outlet 84 of the filter 78 to the inlet 85 of a filter 86 that is the same as the filter 78. The filters 78 and 86 have a National Stock Number (NSN) of 4240-01-161-3710 and are available at the Donaldson Company, Inc. of Minneapolis, Minn. A valved drain line 87 is connected to the plenum 82. A differential pressure detector 88 that is connected at the outlet of filter 86 and monitors pressure relative to ambient and sounds a horn 89 if the differential pressure decreases below a set value. If a filter 78 or 86 dogs, the pressure drops, alarms sound, and all valves are closed. Operations then cease so that filters can be changed and the STAG can go back on line.

The outlet 90 of the filter 86 is connected via a tube 92 and a manually operable valve 94 to an inlet 96 of a vacuum pump 98, and via the tube 92, to a tube 100 that intersects the tube 92 and a manually operable valve 102 to the inlet 104 of a vacuum pump 106.

In order to determine whether the filter 78 is operating properly, a heated valved tube 108 extends from the plenum 82 to a detector 110 that determines whether toxic chemicals have reached an unsafe level in which case an alarm will sound. The detoxified exhaust gas from the detector 110 is conveyed via tube 112 to exit 114.

Detector 110 may be any chemical detector suitable for the chemical samples being analyzed. For chemical warfare gases a flame-photometric detector or a detector such as the MINICAM available from CMS of Birmingham, Ala., can be used.

As better seen in FIG. 2, switches 116 and 118 respectively control the supply of external electric power supplied to a plug 120 to the vacuum pumps 98 and 106, and a battery operated internal uninteruptable power supply (UPS) 122 supplies power for the pumps 98 and 106 by the action of a relay 124 if the external power fails. The temperature controller 47 for the injection port 46, the warning light 50 for the differential pressure detector gauge 48, the temperature indicator 56 for the analytic compartment 2, and the temperature controller 58 for the fan 32 are mounted in a control panel 126 in the back side of the glove box 2.

An advantageous aspect of the invention is the ease and quickness with which the glove box 4 and the filter module 6 may be isolated. The valves 62 and 68 can be manually operated to seal off the glove box 4, and the valves 74, 96 and 104, can be manually operated to seal off the filter module 6.

Various features make for ease in setting-up; dismantling and transporting the STAGS. FIG. 3 shows a cover 125, (not to scale) adapted for enclosing the assembly formed by the analytical compartment 2 and the glove box 4 and which is removably attached thereto by spring claps 127 that fit under its bottom. The cover 125 can serve as a table for supporting the assembly when in use. To reduce the size of the cover 125, the aifiock 36 is designed in any suitable manner to be reversed when not in use so as to be stored inside the glove box 4.

The filter module 6 may be carried for short distances by hand holds 128 and 130 and for long distances by an aluminum pallet assembly 132. The assembly of the analytical compartment 2 and the glove box 4 may be carried for short distances by two slide-out hand lifts on each side, the hand lifts 134,136 and 138 being the only ones visible in FIG. 1, and for long distances by an aluminum pallet assembly 140.

In order to protect the (GC) 8, the (TCD) 10, and the (MSD) 12 during transportation, they are attached to the bottom 142 of the analytical compartment 2 via shock mounted tray assemblies 144 and 146 that can be slid in and out like a drawer.

Although the external corners of the glove box 4 and the analytical compartment 2 are shown as being formed by surfaces meeting at 90°, decontamination is greatly facilitated by making them with a cove shape.

What is claimed is:

1. An analytical glove box system, comprising:
   (a) a sealed analytical enclosure;
   (b) analytical instrumentation mounted within said sealed analytical enclosure;
   (c) a sealed glove box;
   (d) an injection port for said instrumentation mounted in said glove box;
   (e) means for coupling said injection port to said analytical instrumentation;
   (f) an air lock providing access to said glove box;
   (g) an intake port for said glove box;
   (h) an exhaust port for said glove box;
   (i) means for drawing gas from said glove box; and
   (j) means for filtering air drawn from said glove box.

2. An analytical glove box system for identifying sample of toxic materials, comprising:
   (a) a sealed analytical enclosure having chemical analyzing instrumentation mounted within said enclosure;
   (b) a glove box enclosure having an interior;
   (c) an injection port mounted in said glove box and connected to said instrumentation so that said samples can be fed from said glove box enclosure to said analytical instruments;

(d) means for conducting effluent from said instrumentation to said glove box enclosure;

(e) a dual door airlock mounted between ambient air and the interior of said glove box so that said samples can be introduced into said glove box without releasing toxic materials;

(f) first and second openings in said glove box having respective peripheries and including a first glove having a wrist section sealed to the periphery of said first opening, and a second glove having a wrist section sealed to the periphery of said second opening;

(g) an air intake port mounted so as to communicate with said glove box;

(h) a first valve coupled to said air intake port;

(i) an exhaust port for said glove box enclosure;

(j) means for drawing air from said glove box enclosure via said exhaust port so as to maintain a given negative pressure in said glove box enclosure; and (k) means for filtering air drawn from said glove box enclosure.

3. An analytical glove box system as set forth in claim 2, further comprising:

a second valve coupled to said exhaust port for said glove box so that said glove box can be sealed off by closing said second valve for said exhaust port and said first valve coupled to said air intake port.

4. An analytical glove box system as set forth in claim 2, further comprising:

a high pressure alarm coupled to said glove box enclosure, indicating any loss of negative pressure within said glove box with respect to ambient air pressure.

5. An analytical glove box system as set forth in claim 4, wherein said alarm comprises a pressure gauge connected to a warning light and horn.

6. An analytical glove box system as set forth in claim 2, further comprising:

(a) an exhaust fan coupled to said analytical enclosure;

(b) a temperature indicator for said analytical enclosure, said indicator being mounted within said glove box; and (c) means for controlling said exhaust fan, so that a desired temperature is maintained within said analytical enclosure.

7. An analytical glove box system as set forth in claim 2, wherein said filtering means comprises:

first and second filters having respective inlet and outlet ports;

said inlet port of said first filter being coupled to said exhaust port of said glove box enclosure;

a plenum coupled between the outlet port of said first filter and the inlet port of said second filter; and an exhaust pump coupled to the outlet port of said second filter.

8. An analytical glove box system as set forth in claim 7, further comprising:

a toxic substance detector coupled to said plenum.

9. An analytical glove box system as set forth in claim 7, further comprising:

a differential pressure detector coupled to the outlet of said second filter and measuring the pressure at the outlet of said second filter with respect to ambient air pressure.

10. An analytical glove box system as set forth in claim 9, further comprising:

an alarm coupled to said differential pressure detector, so that a warning is given when said filters clog.

11. The analytical glove box system as set forth in claim 2, further including:

means for shock mounting said chemical analyzing instrumentation within said enclosures.

12. The analytical glove box system as set forth in claim 2, further comprising:

a removable cover for an assembly comprised of said sealed analytical enclosure and said glove box enclosures;

whereby said cover can form a work base for said assembly.

* * * * *